United States Patent [19]

Juergensen et al.

[11] Patent Number: 5,549,904
[45] Date of Patent: Aug. 27, 1996

[54] BIOLOGICAL ADHESIVE COMPOSITION AND METHOD OF PROMOTING ADHESION BETWEEN TISSUE SURFACES

[75] Inventors: Kay Juergensen, Murten; Daniel Aeschlimann, Basel; Ernst B. Hunziker, Riedholz, all of Switzerland

[73] Assignee: Orthogene, Inc., San Francisco, Calif.

[21] Appl. No.: 71,528

[22] Filed: Jun. 3, 1993

[51] Int. Cl.$^6$ .............................. A61F 2/02; A61K 38/43; A61K 38/50
[52] U.S. Cl. ................................ 424/423; 514/2; 514/12; 514/21; 514/955; 530/835; 530/840; 530/841; 530/842; 530/846; 530/850
[58] Field of Search ................................ 424/423; 514/2, 514/12, 21, 955; 530/835, 840, 841, 842, 846, 850

[56] References Cited

U.S. PATENT DOCUMENTS

| 4,325,867 | 4/1982 | Eberle et al. | 260/112 B |
| 4,582,794 | 4/1986 | Russell | 435/16 |
| 4,728,643 | 3/1988 | Holick et al. | 514/167 |
| 4,968,713 | 11/1990 | Baldwin et al. | 514/398 |
| 5,037,816 | 8/1991 | Holick et al. | 514/167 |
| 5,270,300 | 12/1993 | Hunziker | 514/12 |

FOREIGN PATENT DOCUMENTS

| 8901512 | 2/1989 | WIPO. |
| 9213565 | 8/1992 | WIPO. |

OTHER PUBLICATIONS

Taylor, D. A. et al., "Novel Transglutaminases for Tissue Glues," Clinical Research, vol. 40, No. 01, 1992, p. 31A.
D. Aeschlimann and M. Paulsson, "Transglutaminases: Protein Cross-Linking Enzymes in Tissues and Body Fluids", Thrombosis and Hemostasis, vol. 71, pp. 402–415 (1994).
T. Kanaji, et al., "Primary Structure of Microbial Transglutaminase from Streptoverticillium sp. Strain s-8112", J. of Biol. Chem., 268:11565–11572 (1993).
J. E. Folk and D. I. Chung, "Molecular and Catalytic Properties of Transglutaminases", Adv. Enzymol., 109–110 and Chapter D., Role of Metal Ions, pp. 133–141 (1973).
Aeschlimann, D. et al: "Cross–Linking of Laminin–Nidogen Complexes . . . " J. Biol Chem 266:15308–15317 (1991).
Arnoczky, S. P. et al: "Microvasculature of the Human Meniscus" Am J Sports Med 10(2):90–95 (1982).
Bauer, M. et al: "Chondral Lesions of the Femoral Condyles . . . " Arthroscopy 4(2):97–102 (1988).
Buckwalter, J. A. et al: "Articular Cartilage: Composition, Structure . . . " reprinted in Articular Cartilage & Knee Joint Function: Basic Science and Arthroscopy, New York, Raven Press (1990).
Carrell, N. A. et al: "Electron Microscopy and Hydrodynamic Properties . . . " J Biol Chem 264(1):551–556 (1989).
Connellan, J. M. et al: "Structural Properties of Guinea Pig Liver . . . " J. Biol Chem 246(4):1093–1098 (1971).
Coutts, R. D., et al: "Rib periochondrial Autografts in Full–Thickness . . . " Chip Orthop 263–273 (1992).
Federico, D. J. et al: "Osteochondritis Dissecans of the Knee: A Historical Review of Etiology & Treatment," Arthroscopy 6(3):190–197 (1990).
Folk, J. E. et al; "The ε–(γ–Glutamyl)Lysine Crosslink and the Catalytic Role of Transglutaminases," Adv Protein Chem 31:1–133 (1977).
Folk, J. E.: "Transglutaminases," Ann Rev Biochem 49:517–531 (1980).

(List continued on next page.)

Primary Examiner—Carlos Azpuru
Attorney, Agent, or Firm—Wood, Herron & Evans, P.L.L.

[57] ABSTRACT

A formulated biological adhesive composition utilizes tissue transglutaminase in a pharmaceutically acceptable aqueous carrier. The tissue transglutaminase is used in an effective catalytic amount to promote adhesion between tissue surfaces upon treatment thereof by catalyzing the reaction between glutaminyl residues and amine donors of the tissue and/or the enzyme. The carrier contains a divalent metal ion such as calcium to promote said reaction.

36 Claims, 5 Drawing Sheets

- NaCl:   0.9% NaCl
- buffer:   0.1 M CaCl2, 0.3 M NaCl, 0.01 M Tris-buffer, pH 7.4
- untreated:   cut surfaces, but without treatment
- tTG:   tissue transglutaminase, 1 mg/ml Gorman, J. J. et al.: "Structural Features of Glutamine Substrates for Transglutaminases," J Biol Chem 25(14):9007–9010 (1984).

Greenberg, C. S. et al.: "Transglutaminases: Multifunctional Cross–Linking Enzymes That Stabilize Tissues," FASEB J 5:3071–3077 (1991).

Hauschka, P. V. et al: Growth Factors in Bone Matrix: "Isolation of Multiple Types by Affinity . . . " J Biol Chem 261(27):12665–12674 (1986).

Homminga, G. N. et al.: "Perichondral Grafting for Cartilage Lesions of the Knee," J Bone Joint Surg (Br) 72–B(6):1003–1007 (1990).

Homminga, G. N. et al.: "Repair of Articular Defects by Perichondrial Grafts: Experiments in the Rabbit," Acta Orthop Scand 60(3):326–329 (1989).

Bowness, J. M. et al: "Identification of a Substrate Site for Liver Transglutaminase . . . " J Biol Chem 262(3):1022–1024 (1987).

OTHER PUBLICATIONS

Ichinose, A. et al.: "Structure of Transglutaminases," J Biol Chem 265(23):13411–13414 (1990).

Ikura, K. et al.: "Amino Acid Sequence of Guinea Pig Liver Transglutaminase From Its cDNA Sequence," Biochemistry 27:2898–2905 (1988).

Itay, S. et al.: "Use of Cultured Embryonal Chick Epiphyseal Chondrocytes as Grafts for Defects in Chick Articular Cartilage," Clin Orthop 220:284–303 (1987).

Jurgensen, K. et al.: "Adhesion Between Cartilage Tissue Surfaces, Connective Tissue Surfaces . . . " M. E. Muller––Institute for Biomechanics, 1–20 (1992).

Mitchell, N. et al.: "Effect of Patellar Shaving in the Rabbit," J Orthop Res 5:388–392 (1987).

Mitchell, N. et al.: "Healing of Articular Cartilage in Intra–Articular Fractures in Rabbits," J Bone and Joint Surg 62–A:628–634 (1980).

Mitchell, N. et al.: "The Resurfacing of Adult Rabbit Articular Cartilage By Multiple Perforations . . . " J. Bone and Joint Surg 58–A:230–233 (1976).

Mitchell, N. et al.: "Effect of Patellar Shaving in the Rabbit," J Orthop Res 5:388–392 (1987).

Mitchell, N. et al.: "Healing of Articular Cartilage in Intra–Articular Fractures in Rabbitts," J Bone and Joint Surg 62–A:628–634 (1980).

Mitchell, N. et al.: "The Resurfacing of Adult Rabbit Articular Cartilage By Multiple Perforations . . . " J Bone and Joint Surg 58–A:230–233 (1976).

Mow, V. C. et al: "Cartilage and Diarthrodial Joints as Paradigms for Hierarchical Materials and Structures," Biomaterials 13(2):67–97 (1992).

Lorand, L. et al: "Transglutaminases," Mol Cell Biochem 58:9–35 (1984).

O'Driscoll, S. W. et al.: "Durability of Regenerated Articular Cartilage Produced by Free Autogenous Periosteal . . . " J Bone & Joint Surg 70–A(4):595–606 (1988).

Pineda, S. J. et al.: "Osteochondral Progenitor Cells Enhance Repair of Large Defects in Rabbit Articular Cartilage," Trans Orthop Res Soc 17(2):598 )1992).

Pridie, K. H.: "A Method of Resurfacing Osteoarthritic Knee Joints," J Bone Joint Surg (Br) 41–B:618–619 (1959).

Schmid, A. et al.: "Results After Cartilage Shaving Studied By Electron Microscopy," Am J Sports Med 15(4);386–387 (1987).

Scott, D. J. et al: "Osteochondritis Dissecans of the Knee in Adults," Clin Orthop 76:82–86 (1990).

Scott, W. N. et al.: "Injuries of the Knee," reprinted in Rockwood and Green's Fractures in Adults, Philadelphia, J. B. Lippincott Company (1991).

Seyedin, S. M. et al.: "Cartilage–Inducing Factor–α: Apparent Identify to Transforming Growth . . . " J Biol Chem 261(13):5693–5695 (1986).

Zapf, J. et al.: "Insulin–Like Growth Factors/Somatomedins: Structure, Secretion, Biological Actions . . . " Horm Res 24:121–130 (1986).

Aeschlimann, D. et al: "Expression of Tissue Transflutaminase in Skeletal Tissues Correlates with Events of Terminal Differentiation of Chondrocytes" J. Cell Biol. vol. 120[6], p.1461 to 1470 (1993).

Gorman, J. J. et al: "Structural Features of Glutamine Substrates for Transfutaminases" J. Biol Chem 256(6): 2715(1981).

Carney, S. L. "Proteoglycans. Carbohydriate Analysis" Oxford, IRL Press (1986).

Schlag, G. et al (Ids) "Fibrin Sealant in Operative Medicine", Traumatology Orthopaedics vol. 7, Sprize Veslag, New York, 1986.

Smilie, I. "Osteochrondritis Dissecans", London, Livingston (1960).

- NaCl: 0.9% NaCl
- buffer: 0.1 M CaCl2, 0.3 M NaCl, 0.01 M Tris-buffer, pH 7.4
- untreated: cut surfaces, but without treatment
- tTG: tissue transglutaminase, 1 mg/ml

FIG. I

- NaCl: 0.9% NaCl
- buffer: 0.1 M CaCl2, 0.3 M NaCl, 0.01 M Tris, pH 7.4
- untreated: cut surfaces, but without treatment
- tTG: tissue transglutaminase, 1 mg/ml

- tTG: tissue transglutaminase, 1 mg/ml
- Tissucol®: two components:
  1. 75-115 mg/ml fibrinogen, 2-9 mg/ml plasma fibronectin, 10-50 U/ml factor XIIIa and 40-120 µg/ml plasminogen.
  2. 4 IU thrombin

- tTG: tissue transglutaminase, 1 mg/ml
- CAC: Chondroitinase AC, 1 U/ml

BIOLOGICAL ADHESIVE COMPOSITION AND METHOD OF PROMOTING ADHESION BETWEEN TISSUE SURFACES

TECHNICAL FIELD OF THE INVENTION

This invention relates to the employment of biological adhesives in surgery. There are many situations within the different surgical specialties where the application of a biological glue would be beneficial. A biological glue can be used to stop a haemorrhage in general surgery, reconstruct nerve ruptures in neurosurgery, adhere skin and cartilage transplants and defects in plastic surgery, treat pneumothorax and/or fistulas in general or thoracic surgery, support vascular and intestinal anastomoses in vascular and general surgery, etc.

In orthopedic surgery, possible applications of a biological sealant include the treatment of chondral—and osteochondral fractures, transplantation of chondral or osteochondral materials, treatment of osteochondritis dissecans, joint fractures, meniscal tears as well as ruptured ligaments, tendons, myotendineous junctions or muscles. Furthermore, the polymerization and adhesion of biomatrix implants, being composed e.g. of collagen, gelatin, fibrinogen, fibrin, or also macromolecules that are not tissue transglutaminase substrates such as polylactates etc. and possibly containing various additives such as cell-attachment proteins, growth factors, cells etc., to tissue defects in order to enhance and stimulate the healing processes. This latter application of the new biological sealant is of a particular importance.

This invention pertains to a formulated biological adhesive composition, its method of preparation and application. The adhesive composition is based on a particular mode of use of tissue transglutaminase (tTG=transglutaminase II=transglutaminase type C) in a pharmaceutically acceptable carrier. The value of the invention has been documented by biomechanical testing of adhesiveness between connective tissue surfaces.

BACKGROUND OF THE INVENTION

Cartilage covers all articulating surfaces and does, due to its unique structure, endow a joint with nearly frictionless motion. The coefficient of friction, defined as $\mu$=frictional force (F)/applied load (W), for articular cartilage in a diarthrodial joint is 0.005–0.02 (human knee). As a comparison, the coefficient of friction for ice on ice is around five times higher (0.01–0.1), Mow, V. C., A. Ratcliffe and A. R. Poole "CARTILAGE AND DIARTHRODIAL JOINTS AS PARADIGMS FOR HIERARCHICAL MATERIALS AND STRUCTURES" Biomaterials, 13(2): 67–97 (1992).

The matrix of articular cartilage consists of 60–80% water (and dissolved ions and gases) by wet weight of articular cartilage and 20–40% structural molecules like collagen, proteoglycans, glycosaminoglycans and glycoproteins. Chondrocytes, the specialized cells in articular cartilage, are embedded in this matrix and occupy only about 10% of the volume and articular cartilage contains neither nerves nor lymphatic vessels nor blood vessels, Buckwalter, J. A., L. C. Rosenberg and E. B. Hunziker, "ARTICULAR CARTILAGE: COMPOSITION, STRUCTURE, RESPONSE TO INJURY, AND METHODS OF FACILITATING REPAIR", reprinted in *ARTICULAR CARTILAGE AND KNEE JOINT FUNCTION: BASIC SCIENCE AND ARTHROSCOPY* New York, Raven Press (1990) and Hunziker, E. B. "STRUKTURMOLEKULE DES KNORPELGEWEBES, DER SEHNEN UND BANDER", Kniegelenk und Kreuzbander, Berlin, Springer (1990).

Two types of articular lesions can be differentiated. First, the chondral or superficial defect; this does not extend to or damage the subchondral bone. The subchondral bone is innervated, contains blood vessels, and connects the articular cartilage to the bone and bone marrow. Superficial cartilage lesions, not extending to the subchondral bone (i. e. partial thickness defects), may appear as a linear-crack type, a stellate fracture, a flap type, a fibrillation type, Bauer, M. and R. W. Jackson "CHONDRAL LESIONS OF THE FEMORAL CONDYLES: A SYSTEM OF ARTHROSCOPIC CLASSIFICATION" Arthroscopy, 4(2):97–102 (1988). Cartilage lesions are often of traumatic origin but do also occur without any obvious cause. Because of the lack of nerve supply, they usually do not cause pain. If symptoms occur, they are detected as delayed swelling of the synovium (the inner side of the joint capsule), with a intermittent locking as a result of a chondral fragment, or as recurrent effusions and crepitus, Scott, W. N. and J. N. Insall "INJURIES OF THE KNEE", reprinted in *ROCKWOOD AND GREEN'S FRACTURES IN ADULTS*, Philadelphia, J. B. Lippincott Company (1991). Such defects are notorious as they do not heal, do not show propensity for repair reactions, and show many similarities to the early stages of degenerative joint diseases, such as osteoarthritis. Secondly, the full-thickness defect; this extends to the subchondral bone, which contains nerves and blood vessels. It results for example from heavy trauma as a crater—or degrading type (Bauer et al, supra), or occurs in late stages of degenerative joint diseases, such as osteoarthritis. A symptom is often severe pain. Bleedings and repair reactions may occur, resulting in a vascularized fibrous type of cartilage which is however not sufficient to support joint function. Such repair tissue very rarely persists (Buckwalter et al, supra).

Currently, still various attempts are made to facilitate cartilage repair in chondral and subchondral defects. One approach is to drill through chondral defects into the subchondral bone which induces bleeding, Pridie, K. H. "A METHOD OF RESURFACING OSTEOARTHRITIC KNEE JOINTS" J Bone Joint Surg (Br) 41-B: 618–619 (1959). Through the bleeding repair reactions are induced and fibrocartilage is formed, but this tissue shows insufficient biomechanical properties and lacks long term persistence, Mitchell, N. and N. Shepard "THE RESURFACING OF ADULT RABBIT ARTICULAR CARTILAGE BY MULTIPLE PERFORATIONS THROUGH THE SUBCHONDRAL BONE" J Bone and Joint Surg 58-A: 230–233 (1976). Resurfacing of articular cartilage defects with periosteal and perichondrial grafts has been evaluated, Coutts, R. D., S. L. Y. Woo, D. Amiel, H. P. Von Schroeder and M. K. Kwan "RIB PERIOCHONDRIAL AUTOGRAFTS IN FULL-THICKNESS ARTICULAR CARTILAGE DEFECTS IN RABBITS" Clin Orthop 263–273 (1992); Homminga, G. N., S. K. Bulstra, P. S. M. Bouwmeester and A. J. Van Der Linden "PERICHONDRAL GRAFTING FOR CARTILAGE LESIONS OF THE KNEE" J Bone Joint Surg (Br) 72-B(6): 1003–7 (1990); Homminga, G. N., T. J. van der Linden, E. A. W. Terwindt-Rouwenhorst and J. Drukker, "REPAIR OF ARTICULAR DEFECTS BY PERICHONDRIAL GRAFTS: EXPERIMENTS IN THE RABBIT" Acta Orthop Scand 60(3): 326–329 (1989) and O'Driscoll, S. W., F. W. Keeley and R. B. Salter "DURABILITY OF REGENERATED ARTICULAR CARTILAGE PRODUCED BY FREE AUTOGENOUS PERIOSTEAL GRAFTS IN MAJOR FULL-THICKNESS DEFECTS IN JOINT SURFACES UNDER THE INFLUENCE OF CON- TINUOUS PASSIVE MOTION" J Bone and Joint Surg 70-A(4): 595–606 (1988). Perichondrium and periosteum are thin connective tissue layers which cover fibrocartilage or bone, respectively. Most investigators suture the perichondrium or periosteum into a subchondral defect, thereby creating additional cartilage damage. Others obtained good results by gluing perichondrium onto chondral defects of rabbits knee joints using a commercial fibrin sealant (Tissucol), Homminga, G. N., T. J. van der Linden, E. A. W. Terwindt-Rouwenhorst and J. Drukker, "REPAIR OF ARTICULAR DEFECTS BY PERICHONDRIAL GRAFTS" Acta Orthop Scand 60(3): 326–329 (1989), an approach that did, however, require a two week immobilization of the joint. Joint immobilization has also been recommended when using fibrin sealant for the fixation of chondral or osteochondral fragments because of the poor resistance of the sealant to shear forces, Claes, L., C. Burri, G. Helbing and E. Lehner "BIOMECHANISCHE UNTERSUCHUNGEN ZUR FESTIGKEIT VERSCHIEDENER KNORPELKLEBUNGEN" Helv Chir Acta 48: 11–13 (1981). A major argument against the use of fibrin sealant is the possible transmission of human pathogenic viruses, e.g., human immune deficiency virus (HIV) and hepatitis B virus. For this reason, fibrin sealants composed of crude fractions of human blood plasma proteins are not permitted for use in the United States.

Removal of fibrillated or irregular cartilage (shaving off) has been evaluated as a therapeutic approach, but it has been shown that shaved articular cartilage of the human knee joint will not regenerate and may even cause an increase of fibrillation and cell necrosis, Schmid, A. and F. Schmid "RESULTS AFTER CARTILAGE SHAVING STUDIED BY ELECTRON MICROSCOPY" Am J Sports Med 15(4): 386–387 (1987). Shaving of the patellar cartilage in rabbits does not lead to significant repair, Mitchell, N. and N. Shepard "EFFECT OF PATELLAR SHAVING IN THE RABBIT" J Orthop Res 5: 388–392 (1987).

The use of cultured fetal chondrocytes embedded in a biomatrix containing fibrinogen, thrombin and additional components, Itay, S., A. Abramovici and Z. Nevo "USE OF CULTURED EMBRYONAL CHICK EPIPHYSEAL CHONDROCYTES AS GRAFTS FOR DEFECTS IN CHICK ARTICULAR CARTILAGE" Clin Orthop 220:284–303 (1987), or of bone-marrow-derived mesenchymal stem cells, Pineda, S. J., T. Goto, V. M. Goldberg and A. I. Caplan "OSTEOCHONDRAL PROGENITOR CELLS ENHANCE REPAIR OF LARGE DEFECTS IN RABBIT ARTICULAR CARTILAGE" Trans Orthop Res Soc 17 (2):598 (1992) as grafts, has been successful in chickens and induced full-thickness repair. It is not known whether successful transplantation of chondrocytes into superficial defects has occured in mammals or humans. The mechanical fixation (i. e. local immobilization) of transplants remains a problem in this approach.

Current treatment of cartilage fractures is often hampered by the failure of the tissue to adhere spontaneously. Stabilization of fragments with screws or Kirschner wires requires repeated surgical intervention, which results in additional trauma and destruction, and in spite of this, stable fixation is frequently not achieved. Cartilage fractures have to be reduced very precisely (best geometrical fit), otherwise fractures will heal through the formation of a fibrocartilage with insufficient biomechanical properties, Mitchell, N. and N. Shepard "HEALING OF ARTICULAR CARTILAGE IN INTRA-ARTICULAR FRACTURES IN RABBITS" J Bone and Joint Surg 62-A: 628–634 (1980).

Osteochondritis dissecans is an osteochondral lesion with an unknown, probably multifactorial etiology. Most patients with a loose osteochondral fragment in the joint have to undergo surgery, as nonoperative treatment has been shown to accelerate degenerative arthritis, Federico, D. J., J. K. Lynch and P. Jokl "OSTEOCHONDRITIS DISSECANS OF THE KNEE: A HISTORICAL REVIEW OF ETIOLOGY AND TREATMENT" Arthroscopy 6(3): 190–197 (1990). The options for fixation of osteochondral fragments include the use of compression-screws, Kirschnet wires, or a compression pinning system (hooked wires, anchoring screws, and bolts), Jakob, R. P. "THE TREATMENT OF OSTEOCHONDRITIS DISSECANS OF THE KNEE JOINT USING A NEW COMPRESSION WIRE SYSTEM" Z Unfallchir Versicherungsmed. 83(2): 104–110 (1990); Scott, D. J. and C. A. Stevenson "OSTEOCHONDRITIS DISSECANS OF THE KNEE IN ADULTS" Clin Orthop 76:82–86 (1990) and Smilie, I. "OSTEOCHONDRITIS DISSECANS", London, Livingston (1960). In most cases, a second operation is required in order to remove the metal. The usefulness of biological sealants in treatment of osteochondritis dissecans has not been evaluated so far.

The human meniscus is a discoid or semilunar slice of cartilage (consisting mainly of circumferentially orientated collagen fibers). It is present between joint surfaces, improves joint congruency and lessens point contact, as e.g. in the knee joint (Scott, W. N. and J. N. Insall, "INJURIES OF THE KNEE", reprinted in *ROCKWOOD AND GREEN'S FRACTURES IN ADULTS*, Philadelphia, J. B. Lippincott Company (1991). The central and inner part of the meniscus consists of an avascular, aneural and alymphatic fibrocartilage, Arnoczky, S. P. and R. F. Warren "MICROVASCULATURE OF THE HUMAN MENISCUS" Am J Sports Med 10(2): 90–95 (1982). Only meniscal tears that occur in the vascular periphery, and that are 3 cm in length or shorter, respond to mechanical suturing. In other types of meniscal tears, the inner meniscal portions are generally excised, a treatment that does in most cases lead to degenerative joint disease, (Scott, W. N. and J. N. Insall "INJURIES OF THE KNEE", reprinted in *ROCKWOOD AND GREEN'S FRACTURES IN ADULTS* Philadelphia, J. B. Lippincott Company (1991)). A method for repairing all types of meniscal tears by use of an effective biological sealant would be of great clinical value. This would minimize, or even prevent, the high frequency of postoperative degenerative joint disease.

A number of substances are known to have the potential of stimulating chondrogenesis. For example, a collagen sponge implant can facilitate chondral repair, Speer, D. P., M. Chvapil, R. G. Volz and M.D. Holmes "ENHANCEMENT OF HEALING IN OSTEOCHONDRAL DEFECTS BY COLLAGEN SPONGE IMPLANTS." Clin Orthop 144: 326–335 (1979). A number of proteins can promote chondrogenesis, like transforming growth factor beta, Seyedin, S. M., A. Y. Thompson and H. Bentz "CARTILAGE-INDUCING FACTOR-α: APPARENT IDENTITY TO TRANSFORMING GROWTH FACTOR-β" J Biol Chem. 261(13): 5693–5695 (1986) and Sporn, M. B., A. B. Roberts and L. M. Wakefieland R. K. Assoiand "TRANSFORMING GROWTH FACTOR-β: BIOLOGICAL FUNCTION AND CHEMICAL STRUCTURE" Science 233: 532–534 (1986), fibroblast growth factor, Zapf, J. and E. R. Froesch "INSULIN-LIKE GROWTH FACTORS/SOMATOMEDINS: STRUCTURE, SECRETION, BIOLOGICAL ACTIONS AND PHYSIOLOGICAL ROLE" Horm Res 24: 121–130 (1986) and insulin-like growth factor, Hauschka, P. V., A. E. Mavrakos and M. D. Iafrati "GROWTH FACTORS IN BONE MATRIX: ISOLATION OF MULTIPLE TYPES BY AFFINITY CHROMATOGRAPHY ON HEPARIN-SEPHAROSE" J Biol Chem 261(27): 12665–12674 (1986).

Further work is required to identify the most useful factors and to find ways to deliver and anchor them into the site of injury (Buckwalter et al, supra). An improved biological sealant could, however, greatly facilitate the clinical usefulness of such bioactive agents.

An effective biological sealant which may be used without risk of virus transmission, leading to hepatitis B or acquired immune deficiency syndrome (AIDS), would indeed open new therapeutic possibilities in all the situations described above.

SUMMARY OF THE INVENTION

This invention is directed to a formulated biological adhesive composition and its method of use. The composition contains tissue transglutaminase in a pharmaceutically acceptable aqueous carrier. The method is practiced by employing the composition containing tissue transglutaminase in an effective catalytic amount (100 µg/ml to 50 mg/ml) to promote adhesion between tissue surfaces upon treatment thereof by catalyzing the reaction between glutaminyl residues and amine donors of the tissue or in the enzyme itself. The carrier also contains a divalent metal ion to promote said reaction.

In a preferred form, the biological adhesive composition contains tissue transglutaminase in a pharmaceutically acceptable carrier having a pH of about 7 to about 8.5, a buffer and calcium ($Ca^{2+}$) ions. Further, the use of tissue transglutaminase does not require the inclusion of a proteolytic enzyme in the formulation and thus limits the risk of tissue damage (as for example induced by thrombin and plasmin present in fibrin sealant, etc.). The sealant composition may optionally contain one or more matrix forming proteins, such as fibronectin, or a growth factor such as transforming growth factor β.

The tissue transglutaminase may be obtained from animal cells and cellular products. Tissue sources from which transglutaminase enzymes may be prepared for use in the biological sealant compositions consist of cells and cellular products including many organs and cell types of the human or animal body such as lung, liver, spleen, kidney, heart muscle, skeletal muscle, eye lens, endothelial cells, erythrocytes, smooth muscle cells, bone and macrophages.

The biological adhesive composition is particularly suited for use in the treatment of tissue surfaces in orthopedic or traumatological surgery. Compositions may also be used in the treatment of biomatrices including cells embedded in a matrix where the matrix may be biodegradable or nonbiodegradable. The biomatrices may also contain naturally occuring or synthetic proteins having transglutaminase substrate sites. Adhesion may be promoted between natural tissue surfaces and a biomatrix-coated implant material. The tissue transglutaminase may be a recombinant DNA tissue transglutaminase and, particularly, where the recombinant DNA has molecular regions that differ from a natural tissue transglutaminase without affecting its promotion of adhesion.

The above features of this invention and other embodiments of the sealant composition and its method of use will be further understood with reference to the following detailed description.

DETAILED DESCRIPTION

A. Tissue Transglutaminase

Sources from which transglutaminase enzymes may be prepared for use in the biological sealant compositions consist of cells and cellular products including many organs and cell types of the human or animal body such as lung, liver, spleen, kidney, heart muscle, skeletal muscle, eye lens, endothelial cells, erythrocytes, smooth muscle cells, bone and macrophages. The tissue source of the enzyme may be selected or specifically adjusted to the individual medical indication. The term "tissue transglutaminase" (tTG=transglutaminase II=transglutaminase type C) or transglutaminase as used herein specifies this form of the enzyme independent of the cellular origin or post translational modifications, K. Ikura, T. Nasu, H. Yokata, Y. Tsuchiya, R. Sasaki, and H. Chiba "AMINO ACID SEQUENCE OF GUINEA PIG LIVER TRANSGLUTAMINASE FROM ITS cDNA SEQUENCE." Biochemistry 27:2898–2905 (1988). The enzyme may be produced by recombinant DNA technology and may be altered in regions not affecting the active site to obtain better conditions for application (e.g., storage stability, method for application, glutaminyl substrate quality, etc.), higher immunologic tolerance, or enzymatic capacity in certain cases.

B. Pharmaceutically Acceptable Carrier or Media

The tissue transglutaminase is formulated in a pharmaceutically acceptable aqueous carrier or media. The carrier contains a buffering agent to maintain the pH in the range of about 7 to about 8.5. A Tris-buffer or HEPES-buffer may be employed. The preferred Tris-buffer is tris (hydroxymethyl) amino methane hydrochloride. Other types of buffers may be used, but it is desirable to exclude carbonate, acetate and phosphate buffers at high concentrations (or in excess over $Ca^{2+}$ ions because of the low solubility of calcium ions in such buffers. Preferably calcium ($Ca^{+2}$) ions are also present in a concentration above 0.5 mM, preferably about 50–100 mM for cartilage, to promote the reaction. Strontium is another example of a divalent metal ion that may be used.

C. Matrix Protein

The biological sealant composition may optionally contain a matrix-forming protein. The protein may be adjusted to the particular application in the amount and nature of the ingredients and is selected from the group consisting of collagen, fibrin, fibrinogen, fibronectin, entactin, osteonectin, osteopontin, thrombospondin, vitronectin, β-lactoglobulin, and casein, and mixtures thereof. In general, any protein may optionally be employed in the sealant composition where it contains one or more amine acceptor sites for the tissue transglutaminasecatalyzed reaction.

D. Growth Factor

The biological adhesive composition may also contain a growth factor selected from the group consisting of transforming growth factor β family, transforming growth factor α family, insulin-like growth factor family, epidermal growth factor, platelet-derived growth factor family, tumor necrosis factor family, fibroblast growth factor family and interleukins.

E. Orthopedic, Traumatological, or Plastic Surgery Applications

The biological adhesive composition may be employed in the treatment of tissue surfaces in orthopedic or traumatological surgery selected from the group consisting of joint fractures, chondral defects, superficial chondral defects (chondral defects), full-thickness defects, osteochondritis dissecans, meniscal tears, ligament tears, tendon tears, muscle lesions, myotendineous junction lesions, cartilage transplantation, bone transplantation, ligament transplantation, tendon transplantation, chondral transplantation, chondro-osseous transplantation, osseous transplantation, skin graft fixation, grafting (repairing) nerves and blood vessels, patching vascular grafts, microvascular blood vessel anastomosis, and treatment of combinations of said tissue surfaces. (See Schlag, G. Rede, H. (Eds.) "FIBRIN SEALANT IN OPERATIVE MEDICINE", Traumatology Orthopaedics Vol. 7. Springe Veslag, N.Y. 1986).

F. Other Applications

The biological adhesive composition may be employed in other applications such as embryo transfer and applications such as for fibrin glue for the promotion of adhesion between a tissue surface and a biomatrix-coated implant material. The biomatrix implants may further contain a naturally occuring or synthetic protein having transglutaminase substrate sites. The matrix may be biodegradable or nonbiodegradable and the adhesive may be for use of cells embedded in the matrix (mesenchymal cells, chondroblasts, chondrocytes, stem cells, etc.). A modification of the method may include the pretreatment of tissue surfaces with digestive enzymes may be used to enhance adhesion. For instance, pretreatment of tissue surfaces with chondroitinase AC or ABC and/or other digestive enzymes to enhance the availability of substrates for the tissue transglutaminase and therefore increase the gluing capacity (See FIG. 4).

MOLECULAR BASIS FOR THE PROPOSED BIOLOGICAL SEALANT

The method and composition of this invention employs crosslinking of tissue surface proteins by tissue transglutaminase under conditions that mimic physiological events and allow sealant action even without the addition of exogenous substrate proteins. It differs from methods based on known commercially available sealants by the employment of tissue transglutaminase rather than factor XIII, the plasma transglutaminase. The biological sealants of this invention give a broader specificity and allow gluing of tissue surfaces by action of the enzyme alone without any other protein additives. The biological sealant has been found to give tissue adhesion which is stable to higher shear forces than those associated with commercially available sealant containing factor XIII.

The key substance in the inventive biological sealant is tissue transglutaminase, an enzyme that catalyses a chemical reaction by which proteins become crosslinked to form network-like polymers. It belongs to a large family of enzymes, designated transglutaminases which have been shown to have a wide distribution amongst tissues and body fluids. Proteins are modified by transglutaminases during many physiological processes, e. g. in fibrin clots during hemostasis and wound healing, in cell membranes of terminally differentiated cells, in various types of extracellular matrices and in the formation of the cornified envelope of epidermis. While the biological function is known only in a few cases, the mechanism of action of transglutaminase is well characterized at the molecular level.

Transglutaminase (EC 2.3.2.13) catalyses a $Ca^{2+}$-dependent acyl-transfer reaction in which new γ-amide bonds are formed between γ-carboxamide groups of peptide-bound glutamine residues and various primary amines (Folk, J. E. "TRANSGLUTAMINASES" Ann Rev Biochem 49: 517–531 (1980); Folk, J. E. and J. S. Finlayson "THE ε-(γ-GLUTAMYL)LYSINE CROSSLINK AND THE CATALYTIC ROLE OF TRANSGLUTAMINASES" Adv Protein Chem 31: 1–133 (1977) and Lorand, L. and S. M. Conrad "TRANSGLUTAMINASES" Mol Cell Biochem 58: 9–35 (1984). A glutamine residue serves as acyl-donor and the most common acyl-acceptors are ε-amino groups of peptide-bound lysine residues (reaction scheme I) or primary amino groups of some naturally occurring (poly) amines, like putrescine or spermidine (reaction scheme II). In the first case the reaction results in the formation of γ-glutamyl-ε-lysine crosslinks either in or between proteins. Reactions following the second scheme result in modifications possibly affecting the biological activity and turnover of the protein but not in polymer formation.

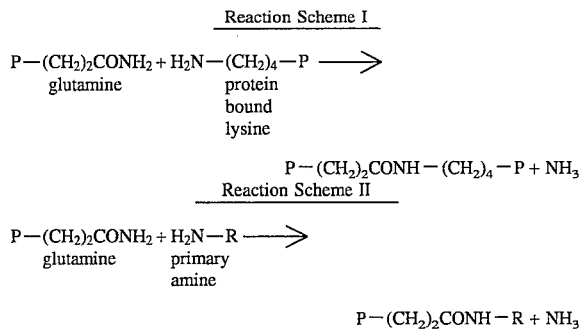

where P=protein and R=organic side chain of variable structure.

The number of proteins acting as glutaminyl substrates is highly restricted, as both primary structure and conformation determine whether a glutamine residue is reactive or not. In contrast, the tolerance to structural differences in acyl-acceptors is considerable, as the only requirement is the presence of a $-(CH_2)_4-NH_2$ group. This explains why both protein bound lysine residues and small primary amines may serve as amine donors. Thus, in a particular tissue only a small subset of proteins are glutaminyl substrates for the enzyme, whereas most proteins of the tissue are able to contribute ε-amino groups of lysine residues to serve as acyl acceptors in the crosslinking reaction. Furthermore, the specificity for different glutaminyl substrates varies depending on the type of transglutaminase. Several types of transglutaminase may recognize a single protein as substrate, but often with different affinity and/or with specificity for different glutamine residues. Certain proteins may serve as substrates only for a single member of the transglutaminase family. Factor XIII, the plasma transglutaminase, is an essential component of the commercially available fibrin sealants, but acts on a much more restricted group of protein-bound glutamines than tissue transglutaminase Gorman, J. J. and J. E. Folk "STRUCTURAL FEATURES OF GLUTAMINE SUBSTRATES FOR TRANSGLUTAMINASES" J Biol Chem 256(6): 2712–2715 (1981) and Gorman, J. J. and J. E. Folk "STRUCTURAL FEATURES OF GLUTAMINE SUBSTRATES FOR TRANSGLUTAMINASES" J Biol Chem 259(14): 9007–9010 (1984). Tissue transglutaminase is a mainly intracellular enzyme with a broad tissue distribution, Greenberg, C. S., P. J. Birckbichler and R. H. Rice "TRANSGLUTAMINASES: MULTIFUNCTIONAL CROSS-LINKING ENZYMES THAT STABILIZE TISSUES" FASEB J5: 3071–3077 (1991).

The sealant of this invention employs tissue transglutaminase rather than factor XIII, a major advantage being that its broad substrate specificity gives a stronger adhesion. Factor XIII exists as a tetramer, $a_2b_2$ (Mr~320'000), composed of a dimer of the catalytic a-subunit (Mr~83'000 each) and two regulatory b-subunits (Mr~S0'000) when circulating in the blood plasma, or as a dimer of only the a-subunit in, e. g. platelets, leukocytes and placenta Carrell, N. A., H. P. Erickson and J. McDonagh "ELECTRON MICROSCOPY AND HYDRODYNAMIC PROPERTIES OF FACTOR XIII SUBUNITS" J Biol Chem 264(1): 551–556 (1989).

The a-subunit of factor XIII has a high degree of sequence homology to tissue transglutaminase but the proteins are derived from different genes, Ichinose, A., R. E. Bottenus and E. W. Davie "STRUCTURE OF TRANSGLUTAMINASES" J Biol Chem 265(23):13411–13414 (1990). Factor XIII is a zymogen, which is activated to factor XIIIa by thrombin cleavage and the following $Ca^{+2}$ dependent dissociation into active a-subunits and inactive b-subunits. The commercially available fibrin sealants are composed of a partially purified fraction of human blood plasma containing the active agents factor XIII, fibrinogen, fibronectin, thrombin, $CaCl_2$.

The abundant tissue transglutaminase is a monomeric globular protein with a molecular mass of about 77'000 (Greenberg et al, Supra and Ichinose, et al, supra) and does, in contrast to factor XIII, not require proteolytic activation. This property makes reproducible applications easier. A number of agents like transforming growth factor β and insulin-like growth factor have previously been described to stimulate chondrogenesis and may be applied in concert with the inventive sealant to achieve optimal regeneration. We have recently shown that tissue transglutaminase is expressed in a variety of cartilages. Aeschlimann, D., Wetterwald, A., Fleisch, H., and Paulsson, M. "EXPRESSION OF TISSUE TRANSGLUTAMINASE IN SKELETAL TISSUES CORRELATES WITH EVENTS OF TERMINAL DIFFERENTIATION OF CHONDROCYTES", J Cell Biol, Vol. 120[6], page 1461 to 1470 (1993). Tissue transglutaminase is likely to catalyze physiological crosslinks in cartilage, and in this respect the inventive sealant mimics a naturally occurring process. As a consequence both the enzyme and its reaction products occur in normal cartilage and are unlikely to be toxic. Transglutaminases catalyze protein crosslinking during formation of the cornified envelope forming the superficial layer of the epidermis, Thacher, S. M. and R. H. Rice "KERATINOCYTE-SPECIFIC TRANSGLUTAMINASE OF CULTURED HUMAN EPIDERMAL CELLS: RELATION TO CROSS-LINKED ENVELOPE FORMATION AND TERMINAL DIFFERENTIATION" Cell 40: 685–695 (1985). As the massive production of crosslinks does not induce an immunological response in the skin, it appears that the products formed by tissue transglutaminases are not immunogenic.

As an important prerequisite for application of the (tTG) enzyme in the highly collagenous skeletal tissues, collagens expressed in bone and tendon, type III (Bowness et al, 1987), and in cartilage, type II (Aeschlimann et al, 1993, supra), are substrates for the tissue transglutaminase enzyme. The observation that several other extracellular substrate proteins are intimately associated with the vascular endothelium like entactin, Osteonectin, (Aeschlimann, D. and M. Paulsson "CROSS-LINKING OF LAMININ-NIDOGEN COMPLEXES BY TISSUE TRANSGLUTAMINASE" J Biol Chem 266: 15308–15317 (1991); Aeschlimann, D., Wetterwald, A., Fleisch, H., and Paulsson, M. "EXPRESSION OF TISSUE TRANSGLUTAMINASE IN SKELETAL TISSUES CORRELATES WITH EVENTS OF TERMINAL DIFFERENTIATION OF CHONDROCYTES" J Cell Biol (1993), in press), vitronectin, fibronectin and fibrin(ogen) (Greenberg, C. S., P. J. Birckbichler and R. H. Rice "TRANSGLUTAMINASES: MULTIFUNCTIONAL CROSS-LINKING ENZYMES THAT STABILIZE TISSUES" FASEB J.5: 3071–3077 (1991)) extends the potential application range of tissue transglutaminase to the repair of vascular lesions.

EXAMPLES

Figure 1:
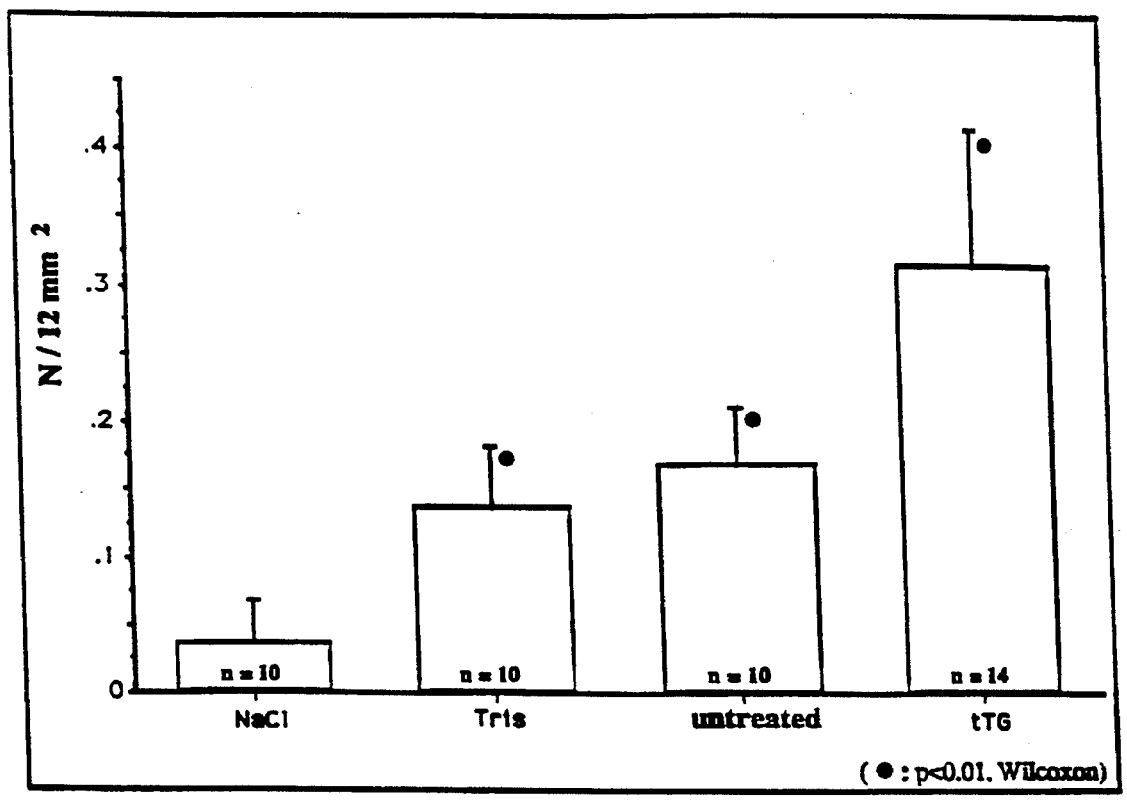
FIG. 1 demonstrates the adhesive effect of tTG on cartilage tissue with an incubation time of 10 minutes.

An in vitro system for the quantitative evaluation of the adhesive strength of biological glues has been developed to be able to compare the adhesive strength obtained with commercially available formulations to that created by the biological sealant of this invention.

Tissue transglutaminase (tTG) was purified from guinea pig liver by means of DEAE-cellulose chromatography of liver homogenate supernatant, followed by protamine precipitation of the enzyme, selective extraction with ammonium sulfate solution, and rechromatography over a molecular sieve column, Connellan, J. M., S. I. Chung, N. K. Whetzel, L. M. Bradley and J. E. Folk "STRUCTURAL PROPERTIES OF GUINEA PIG LIVER TRANSGLUTAMINASE" J Biol Chem 246(4): 1093–1098 (1971). tTG was pooled and concentrated to 1 mg/ml in 10 mM Tris/acetate (pH 6.0), containing 1 mM EDTA and 150 mM NaCl, Aeschlimann, D. and M. Paulsson "CROSS-LINKING OF LAMININ-NIDOGEN COMPLEXES BY TISSUE TRANSGLUTAMINASE" J Biol Chem 266: 15308–15317 (1991).

Tissue transglutaminase was compared to a commercially available fibrin glue (Tissucol) and three other types of controls (NaCl-solution, Tris-reaction buffer and incubation with no treatment). Tissucol consists of two solutions which are mixed prior to application. One part consists of 75–115 mg/ml fibrinogen, 2–9 mg/ml plasma fibronectin, 10–50 U/ml factor XIII and 40–120 μg/ml plasminogen. The other one is made up of 4 IU thrombin in 53 mM $CaCl_2$. After heating to 37° C. and mixing, the two components are applied to the cartilage surfaces. Tissue transglutaminase glue consists of two solutions: A) tissue transglutaminase (1 mg/ml in 10mMTris/acetate, pH 6.0, 150 mM NaCl, 1 mM EDTA) and B) Tris reaction buffer (0.1M $CaCl_2$ in 10 mM Tris/HCl, pH 7.4, 300 mM NaCl), which are applied to separate tissue surfaces and are mixed by joining the two tissue surfaces. A 0.9% NaCl solution, Tris reaction buffer and not treated cartilage surfaces were used as controls.

Pretreatment with 4 μl Chondroitinase AC (CAC) (Sigma), dissolved in phosphate-buffered saline (GIBCO) to an activity of 1 U/ml, on each cartilage surface was performed at 37° C. in a wet chamber for 5 minutes, followed by thorough rinsing with phosphate-buffered saline and careful drying with cellucotton. This pretreatment lead to a depolymerisation of glycosaminoglycans (chondroitin 4-sulphate and chondroitin 6-sulphate) and is therefore likely to have made accessible more substrate sides, Carney, S. L. "PROTEOGLYCANS. CARBOHYDRATE ANALYSIS" Oxford, IRL Press (1986).

Cartilage-bone cylinders with a diameter of 3.9 mm were obtained with a myelotomy drill (Institute Straumann, Switzerland) from a bovine shoulder 10–20 hours after slaughter. 50% of the cartilage thickness was cut off perpendicularly to the long axis of the cylinder with a razor blade.

The surfaces were treated with 4 μl tTG solution and 4 μl Tris reaction buffer, one drop of fibrin glue or 8 μl of the control solutions or left untreated. The two cartilage cylinders were immediately joined at their cut surfaces and an 80 g weight was applied vertically while the assembly was incubated at 37° C. in a humidified chamber (humidity 50 or 80%) for 10 or 15 minutes.

A controlled, linear, ramped shear force (0.27 N/s) was applied to the top cartilage cylinder. The shear force was regulated via a signal generator (wavetech) and an amplifier, exerted by an electromagnetic coil and a ferromagnetic bar, and measured with a specially designed load cell (precision $1.0 \times 10^{-3}$ N). The load cell was connected with a dynamic strain gauge amplifier (DMD 20 A, Hottinger Baldwin Messtechnik, Switzerland). 720 values in 3 seconds were recorded on a data logger (Mikromec, Suprag, Switzerland), from which they were transmitted to a computer (Macintosh LC). In parallel with the digitalization of the resulting force the input signal (linear up ramp) and the measured values can be visualized on an oscilloscope.

Application of the tTG to exposed surfaces of cylindrical cartilage tissue examples produced a much higher adhesive effect than in the control groups where only NaCl-solution, Tris reaction buffer or no solution was applied ($p<0.01$, Wilcoxon signed-rank test) (FIG. 1).

Figure 2:
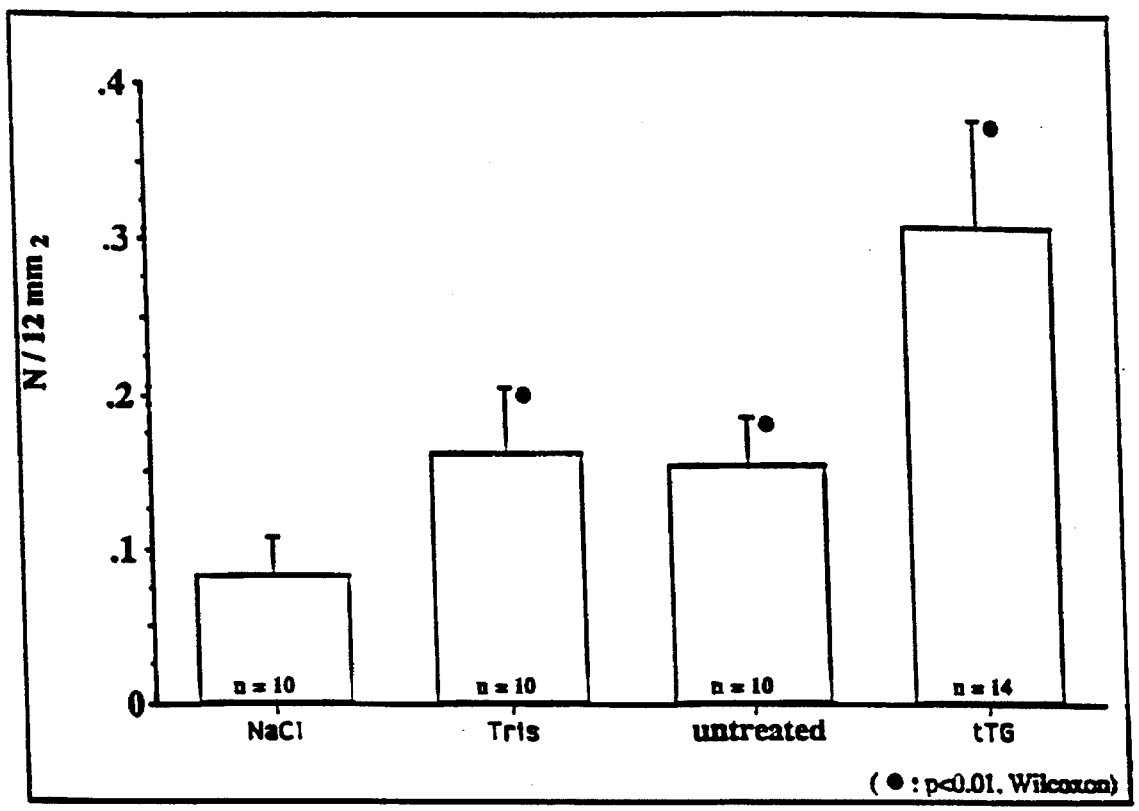
FIG. 2 demonstrates the adhesive effect of tTG on cartilage tissue with an incubation time of 15 minutes.
Figure 3:
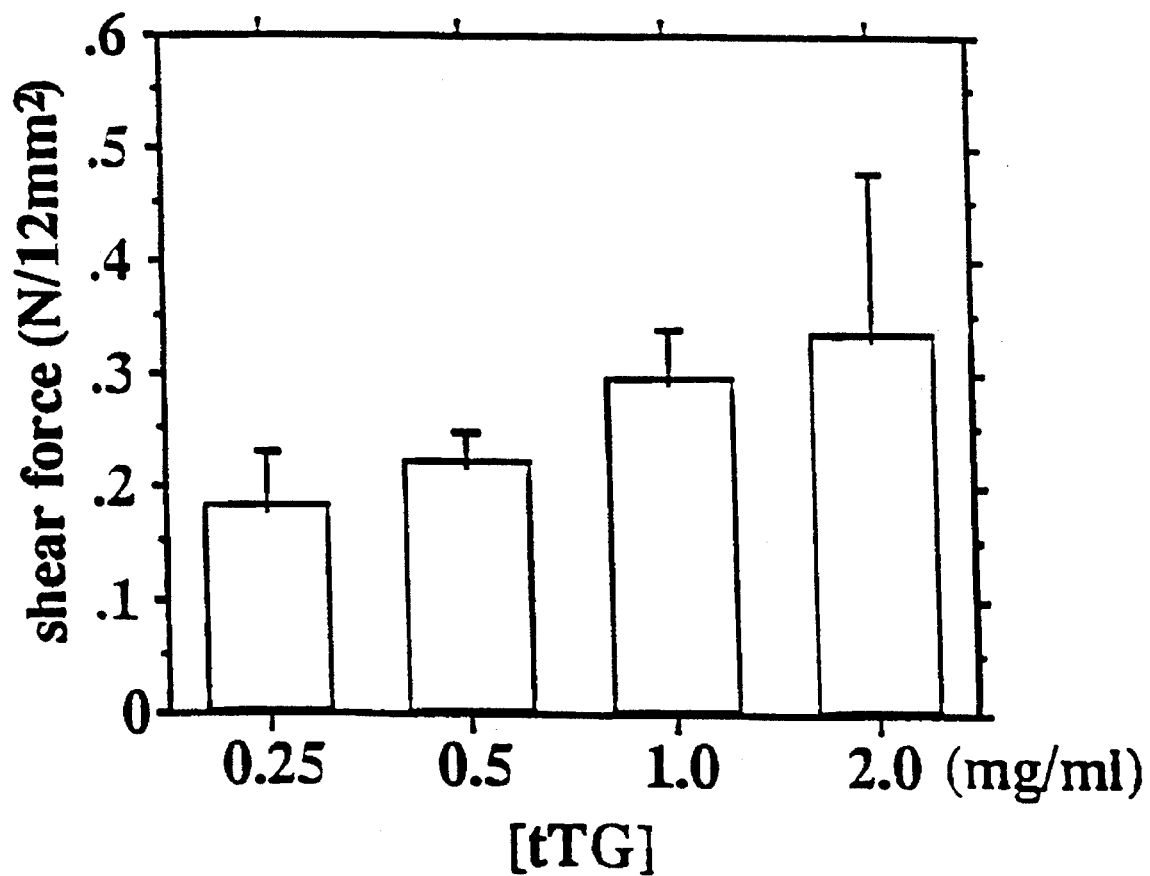
FIG. 3 demonstrates the adhesive effect dependent upon concentration of tTG.

The same effect resulted after increasing the incubation time from 10 minutes (FIG. 1) to 15 minutes (FIG. 2), although the shear force, especially in the NaCl group, showed a tendency to increase. Moreover, the adhesive effect produced was dependent on the concentration of tissue transglutaminase (see FIG. 3).

Figure 4:
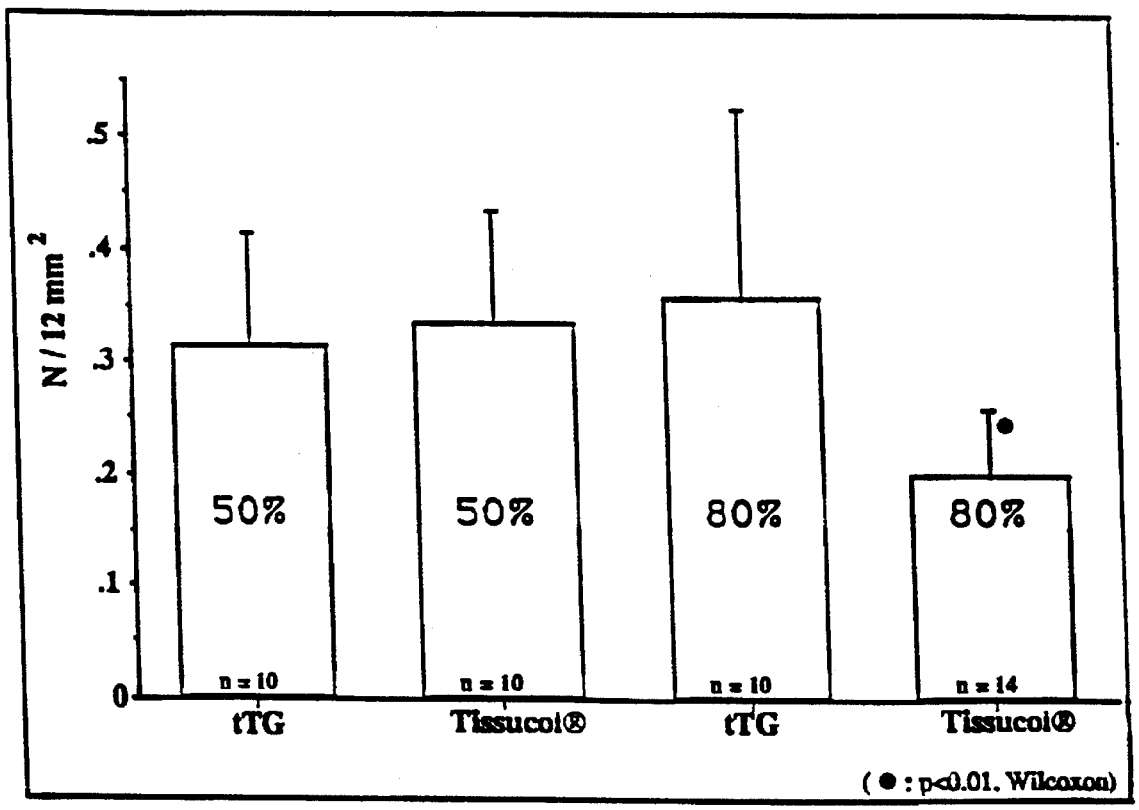
FIG. 4 demonstrates a comparison of the adhesive effect of tTG with Tissucol®.
Figure 5:
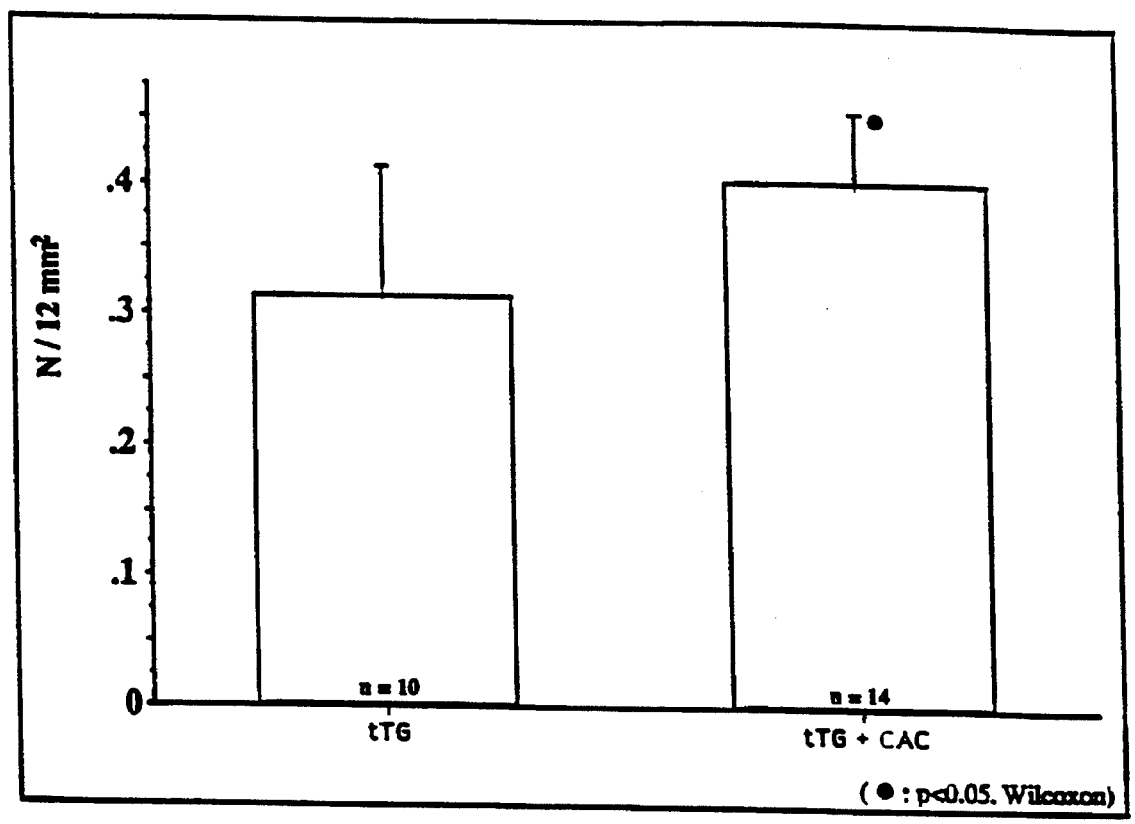
FIG. 5 demonstrates the sealant effect of tTG with prior application of chondroitinase AC.

A comparison of tTG with Tissucol showed a comparative gluing capacity at 50% relative humidity, while much of the adhesive effect of Tissucol (but not of tTG) was lost when relative humidity was raised to 80% (FIG. 4). The sealant effect of tTG with prior application of chondroitinase AC is shown in FIG. 5.

Other modifications or embodiments of this invention will be understood to a person of ordinary skill in this art in view of the above description without departing from the scope of this invention.

What is claimed is:

1. A formulated biological adhesive composition comprising tissue transglutaminase and a pharmaceutically acceptable carrier, said tissue transglutaminase in an effective amount to promote adhesion upon treatment of tissue in the presence of a divalent metal ion.

2. The biological adhesive composition of claim 1 having a pH of about 7 to about 8.5 and a buffering agent.

3. The biological adhesive composition of claim 2 wherein said divalent metal ion is selected from the group consisting of calcium and strontium.

4. The biological adhesive composition of claim 1 wherein said divalent metal ion is calcium.

5. The biological adhesive composition of claim 4 wherein said calcium is present in an amount in the range of about 0.5 mM to about 100 mM.

6. The biological adhesive composition of claim 1 wherein said tissue transglutaminase is obtained from an aggregate of animal cells and cellular products.

7. The biological adhesive composition of claim 1 wherein said tissue transglutaminase is obtained from a tissue source selected from the group of cells and cellular products consisting of lung, liver, spleen, kidney, heart muscle, skeletal muscle, eye lens, endothelial cells, erythrocytes, smooth muscle cells, bone and macrophages to promote the adhesion of tissue surfaces correspondingly selected from said tissue group.

8. The biological adhesive composition of claim 1 containing an additional protein.

9. The biological adhesive composition of claim 8 wherein said protein is selected from the group consisting of collagen, fibrin, fibrinogen, fibronectin, entactin, osteonectin, osteopontin, thrombospondin, vitronectin, β-lactoglobulin, and casein, and mixtures thereof.

10. The biological adhesive composition of claim 1 containing a growth factor.

11. The biological adhesive composition of claim 10 wherein said growth factor is selected from the group consisting of transforming growth factor β family, transforming growth factor α family, insulin-like growth factor family, epidermal growth factor, platelet-derived growth factor family, tumor necrosis factor family, fibroblast growth factor family and interleukins.

12. The biological adhesive composition of claim 1 wherein said tissue transglutaminase is a recombinant DNA tissue transglutaminase.

13. The biological adhesive of claim 12 wherein said recombinant DNA has altered molecular regions without affecting the active site in its promotion of adhesion.

14. The biological adhesive composition of claim 1 for use in the treatment of tissue selected from the group consisting of joint fractures, chondral defects, superficial chondral defects, full-thickness defects, osteochondritis dissecans, meniscal tears, ligament tears, tendon tears, muscle lesions, myotendineious junction lesions, cartilage transplantation, bone tissue transplantation, ligament transplantation, tendon transplantation, chondral transplantation, chondro-osseous transplantation, skin graft fixation, grafting or repairing nerves and blood vessels, patching vascular grafts, and microvascular blood vessel anastomosis.

15. The biological adhesive composition of claim 1 wherein said tissue comprises a biomatrix having transglutaminase substrate sites and containing cells or an embryo transfer system.

16. The biological adhesive composition of claim 1 for use in the treatment of biomatrix implants further containing a naturally occurring or synthetic protein having transglutaminase substrate sites.

17. The biological adhesive composition of claim 16 wherein said protein is selected from the group consisting of collagen, fibrin, fibrinogen, fibronectin, entactin, osteonectin, osteopontin, thrombospondin, vitronectin, β-lactoglobulin, casein, and mixtures thereof.

18. The biological adhesive composition of claim 1 for use in promoting the adhesion between tissue and a biomatrix-coated implant material.

19. The biological adhesive composition of claim 18 wherein said tissue is selected from the group consisting of epithelia, parenchymatous organs, connective or nervous tissue, muscle, cartilage, skin, tendon, ligament, bone, lung, liver, spleen, kidney, heart muscle, skeletal muscle, eye lens, endothelial cells, smooth muscle cells and biomatrix to promote the adhesion of tissue correspondingly selected from said tissue group.

20. A formulated biological adhesive composition comprising tissue transglutaminase and a pharmaceutically acceptable aqueous carrier, said tissue transglutaminase in an amount of about 100 µg/ml to about 50 mg/ml to promote adhesion upon treatment of tissue, said pharmaceutically acceptable aqueous carrier containing calcium ions in a concentration above about 0.5 mM, said composition having a pH of about 7 to about 8.5 and a buffering agent.

21. The biological adhesive composition of claim 20 wherein said tissue transglutaminase is obtained from an aggregate of animal cells and cellular products.

22. The biological adhesive composition of claim 20 wherein said tissue transglutaminase is obtained from a tissue source selected from the group of cells and cellular products consisting of lung, liver, spleen, kidney, heart muscle, skeletal muscle, eye lens, endothelial cells, erythrocytes, smooth muscle cells, bone and macrophages to promote the adhesion of tissue surfaces correspondingly selected from said tissue group.

23. The biological adhesive composition of claim 20 containing an additional protein.

24. The biological adhesive composition of claim 23 wherein said protein is selected from the group consisting of collagen, fibrin, fibrinogen, fibronectin, entactin, osteonectin, osteopontin, thrombospondin, vitronectin, β-lactoglobulin, and casein, and mixtures thereof.

25. The biological adhesive composition of claim 20 containing a growth factor.

26. The biological adhesive composition of claim 25 wherein said growth factor is selected from the group consisting of transforming growth factor β family, transforming growth factor α family, epidermal growth factor, platelet-derived growth factor family, tumor necrosis factor family, fibroblast growth factor family and interleukins.

27. The biological adhesive composition of claim 20 wherein said tissue transglutaminase is a recombinant DNA tissue transglutaminase.

28. The biological adhesive composition of claim 20 for use in the treatment of tissue selected from the group consisting of joint fractures, chondral defects, superficial chondral defects, full-thickness defects, osteochondritis dissecans, meniscal tears, ligament tears, tendon tears, muscle lesions, myotendineious junction lesions, cartilage transplantation, bone tissue transplantation, ligament transplantation, tendon transplantation, chondral transplantation, chondro-osseous transplantation, skin graft fixation, grafting or repairing nerves and blood vessels, patching vascular grafts, and microvascular blood vessel anastomosis.

29. A formulated biological adhesive composition comprising tissue transglutaminase and a pharmaceutically acceptable aqueous carrier, said tissue transglutaminase in an amount of about 100 μg/ml to about 50 mg/ml to promote adhesion upon treatment of tissue, said pharmaceutically acceptable aqueous carrier containing calcium ions in a concentration above about 0.5 mM, wherein said tissue comprises a biomatrix having transglutaminase substrate sites and containing cells or an embryo transfer system.

30. A formulated biological adhesive composition comprising tissue transglutaminase and a pharmaceutically acceptable aqueous carrier, said tissue transglutaminase in an amount of about 100 μg/ml to about 50 mg/ml to promote adhesion upon treatment of tissue, said pharmaceutically acceptable aqueous carrier containing calcium ions in a concentration above about 0.5 mM, for use in the treatment of biomatrix implants further containing a naturally occurring or synthetic protein having transglutaminase substrate sites.

31. The biological adhesive composition of claim 30 wherein said protein is selected from the group consisting of collagen, fibrin, fibrinogen, fibronectin, entactin, osteonectin, osteopontin, thrombospondin, vitronectin, β-lactoglobulin, casein, and mixtures thereof.

32. The biological adhesive composition of claim 20 for use in promoting the adhesion between tissue and a biomatrix-coated implant material.

33. The biological adhesive composition of claim 32 wherein said tissue is selected from the group consisting of epithelia, parenchymatous organs, connective or nervous tissue, muscle, cartilage, skin, tendon, ligament, bone, lung, liver, spleen, kidney, heart muscle, skeletal muscle, eye lens, endothelial cells, smooth muscle cells and biomatrix to promote the adhesion of tissue correspondingly selected from said tissue group.

34. The biological adhesive of claim 1 having a pH of about 7 to about 8.5, a divalent metal ion, and a buffering agent in an aqueous medium.

35. The biological adhesive composition of claim 1 wherein said tissue is selected from the group consisting of epithelia, parenchymatous organs, connective or nervous tissue, muscle, cartilage, skin, tendon, ligament, bone, lung, liver, spleen, kidney, heart muscle, skeletal muscle, eye lens, endothelial cells, smooth muscle cells and biomatrix to promote the adhesion of tissue correspondingly selected from said tissue group.

36. The biological adhesive composition of claim 1 wherein said tissue transglutaminase is in an amount of about 100 μg/ml to about 50 mg/ml.

\* \* \* \* \*